United States Patent [19]

Masuda

[11] Patent Number: 5,575,760
[45] Date of Patent: Nov. 19, 1996

[54] ROLLER THERAPEUTIC APPLIANCE

[75] Inventor: Isamu Masuda, Fukuoka, Japan

[73] Assignee: Nihon Kenko Zoushin Kenkyukai Corporation, Fukuoka, Japan

[21] Appl. No.: 367,638

[22] Filed: Jan. 3, 1995

[30] Foreign Application Priority Data

Dec. 15, 1994 [JP] Japan .................................. 6-333963

[51] Int. Cl.[6] .................................................. A61H 15/00
[52] U.S. Cl. ............................ 601/19; 601/119; 601/120
[58] Field of Search ............................ 601/118–123, 15, 601/18, 19; 600/9, 15

[56] References Cited

U.S. PATENT DOCUMENTS

| | | | |
|---|---|---|---|
| 444,597 | 1/1891 | Lichtenstadt | 601/119 X |
| 1,722,866 | 7/1929 | Snyder | 601/15 X |
| 2,461,413 | 2/1949 | Dirand | 601/120 |
| 3,943,912 | 3/1976 | Nakayama | 600/15 |
| 4,622,956 | 11/1986 | Nesheim | 601/115 |
| 4,727,857 | 3/1988 | Hörl | 600/15 |
| 4,744,350 | 5/1988 | Sato | 601/15 X |
| 4,945,900 | 8/1990 | Masuda | 601/120 |
| 5,123,406 | 6/1992 | Masuda | 601/120 X |
| 5,137,507 | 8/1992 | Park | 600/9 X |
| 5,139,014 | 8/1992 | Chang | 601/19 X |
| 5,143,056 | 9/1992 | Yih-Jong | 601/121 X |

FOREIGN PATENT DOCUMENTS

| | | | |
|---|---|---|---|
| 2510173 | 9/1976 | Germany | 600/9 |
| 2733982 | 2/1979 | Germany | 600/15 |
| 1540825 | 2/1990 | U.S.S.R. | 601/15 |
| 2190844 | 12/1987 | United Kingdom | 600/9 |

Primary Examiner—Robert A. Hafer
Assistant Examiner—Brian E. Hanlon
Attorney, Agent, or Firm—Jordan and Hamburg

[57] ABSTRACT

A roller therapeutic appliance has a pressure roller of an elastic material rotatably disposed in a center portion of an operational axis having grips at both ends. An annular magnetic field generating source is embedded adjacent an outer periphery of the pressure roller, which contacts with a human body. The pressure roller is applied and rotated with pressure on a diseased part of the patient. A pressing force due to the pressure roller and also a magnetic field due to the magnetic field generating source embedded in the pressure roller act on the diseased part, thereby imparting both a massaging effect and a magnetic therapeutic effect. Moreover, the annular magnetic field generating source can easily be embedded a predetermined depth and at predetermined positions in the pressure roller is not exposed on the surface of the pressure roller.

3 Claims, 9 Drawing Sheets

ROLLER THERAPEUTIC APPLIANCE

TECHNICAL FIELD

This invention relates to a roller therapeutic appliance which performs massage and magnetic therapy by applying and rotating a pressure roller, supported on an operation axis, on a diseased part of the patient's body and to a method of fabricating it.

BACKGROUND ART

Conventionally, a roller therapeutic appliance has a pressure roller composed of elastic material, like rubber, which is rotatably disposed via bearings in a center portion of an operation axis provided with grips at both ends. When this roller therapeutic appliance is used, the patient or another person grasps the grips at both ends of the operation axis, applies pressure with the pressure roller and rotates the pressure roller on a diseased part of the patient's body.

However, the roller therapeutic appliance of this type only softens muscles externally by a pressing force, and thus only has a meager therapeutic effect.

When a magnetic field is externally applied to a human body, the circulation of the blood improves and stiffness is alleviated. These magnetic therapeutic effects are widely appreciated.

There have been attempts to provide a roller therapeutic appliance which can give not only a massaging effect, but also a magnetic therapeutic effect by embedding a plurality of permanent magnets along an outer peripheral surface of the pressure roller.

However, it is difficult to embed a permanent magnet at a predetermined depth into a predetermined position, because the pressure roller of the roller therapeutic appliance is made by molding elastic material, such as rubber. Thus, there is a high occurrence of defective rollers which have a part of the permanent magnet exposed from the surface of the pressure roller.

OBJECTS OF THE INVENTION

The object of the present invention is to provide a roller therapeutic appliance which is easy to make and has an excellent therapeutic effect. The roller therapeutic appliance is made by embedding an annular magnetic field generating source into a pressure roller to generate a magnetic field.

SUMMARY OF THE INVENTION

A roller therapeutic appliance in which a pressure roller composed of elastic material is rotatably disposed in a center portion of an operational axis having grips at both ends. The roller has an annular magnetic field generating source embedded adjacent an outer periphery of the pressure roller, which contacts a human body.

According to the invention, the roller therapeutic appliance is grasped by the grips at both ends of the operation axis, and the pressure roller is applied and rotated with pressure on a diseased part of the patient. Using the roller not only results in a pressing force due to the pressure roller, but also a magnetic field due to the magnetic field generating source embedded in the pressure roller acting on the diseased part. Thus, both a massaging effect and a magnetic therapeutic effect can be obtained. Moreover, since the annular magnetic field generating source is embedded adjacent the outer periphery of the pressure roller, the parts for generating the magnetic field can easily be embedded in a predetermined depth in a predetermined position and will not be exposed on the surface of the pressure roller.

In a preferable embodiment, the pressure roller has a constricted part in the center portion and the magnetic field generating sources are embedded in both sides of the roller around the constricted part. When the pressure roller is pressed on the back of a human body, the constricted part is just positioned above the spine of the body, and pressure and a magnetic field can be exerted on muscles on both sides of the spine.

In another embodiment of the pressure roller, the roller is disk-shaped and the annular magnetic field generating source is embedded adjacent the outer periphery of the roller. In this case, the outer peripheral surface of the disk-shaped pressure roller contacts the human body, so a pressing force and a magnetic field act on one portion of the human body. Therefore, the pressure roller is suitable for massage and magnetic therapy of legs or the like.

Moreover, if a plurality of small protrusions are provided at regular intervals along the periphery of the pressure roller, which contacts a human body, a diseased part can be locally pressed and stimulated by these small protrusions.

Preferably, the magnetic field generating source is made by embedding a plurality of permanent magnets, at regular intervals, in a peripheral portion of a non-magnetic metal ring. This configuration facilitates the fabrication of the magnetic field generating source and eliminates concern that the permanent magnets might fall out of the metal ring, even when the appliance is repeatedly used.

Instead of the above configuration, if an annular permanent magnet magnetized along the outer periphery of the ring is used as a magnetic field generating source, the fabrication cost of the field generating source is decreased.

The inventive method of fabricating a roller therapeutic appliance proceeds by the following steps:

a rod-shaped jig is inserted into an inner hole of an annular magnetic field generating source and the annular magnetic field generating source is supported on this jig:

the annular magnetic field generating source supported on the jig and elastic material are molded together to embed the magnetic field generating source in the elastic material and pressurized while applying heat;

the jig is pulled out from the molded pressure roller; and bearings are fitted into the inner hole of the pressure roller, and an operation axis is inserted into the bearings, thereby the pressure roller is rotatably supported at the center portion of the operation axis.

According to the above-mentioned method of fabricating the roller therapeutic appliance, the annular magnetic field generating source is supported on the rod-shaped jig, and then the annular magnetic field generating source on the rod-shaped jig and rubber material are molded together between an upper die and a lower die and pressed. As a result, the pressure roller is molded with the magnetic field generating source embedded therein. Thus, the magnetic field generating source can be easily and correctly positioned and embedded. This facilitates the fabrication of the roller therapeutic appliance, as well as eliminates concern over producing defective rollers with an exposed magnetic field generating source.

3

DETAILED DESCRIPTION OF THE INVENTION

Figure 1:
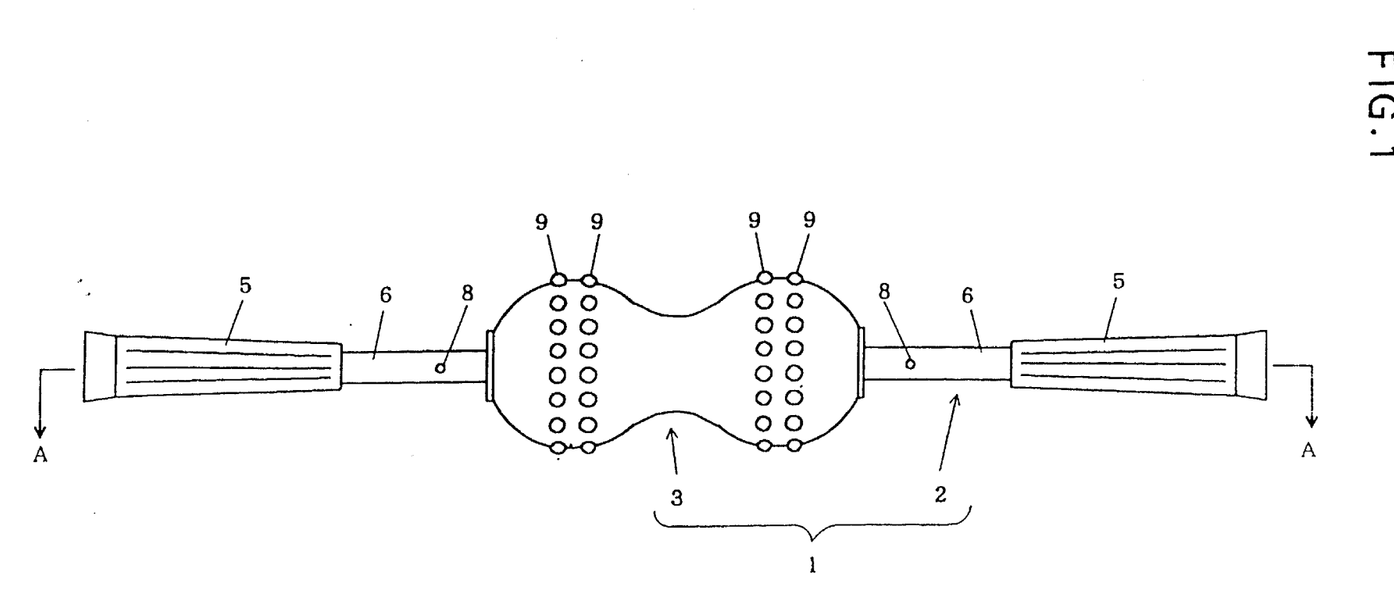
FIG. 1 is a front view of a roller therapeutic appliance of the first embodiment of the present invention.

FIG. 1 shows a roller therapeutic appliance of the first embodiment of the present invention.

Figure 2:
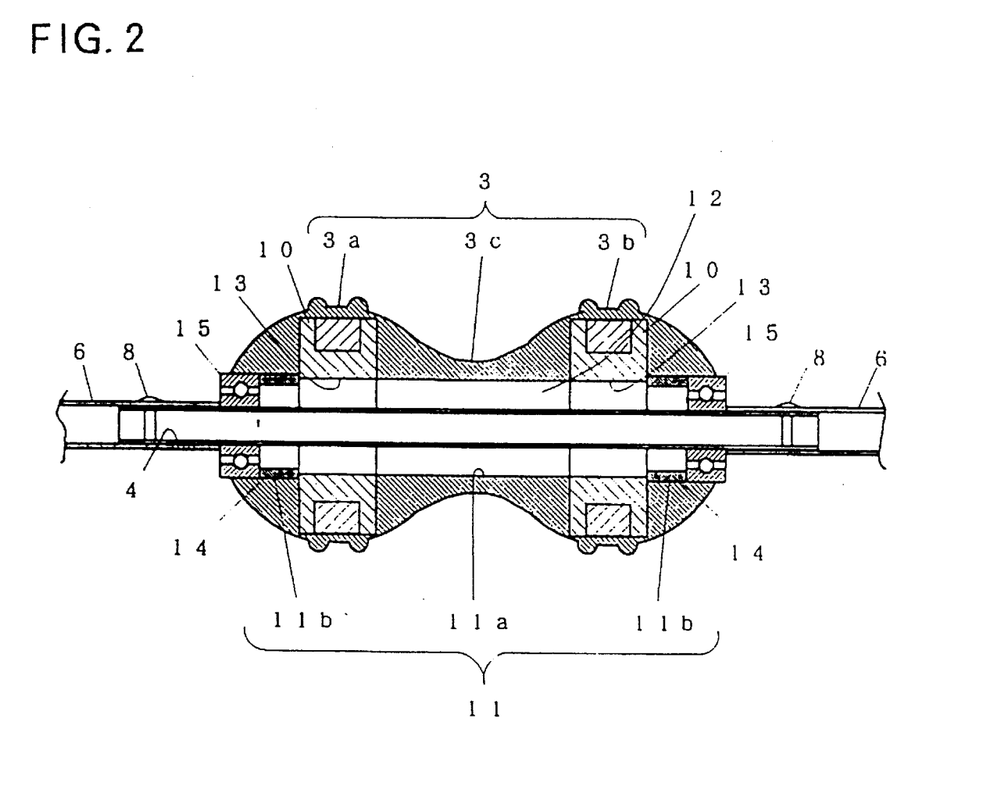
FIG. 2 is a sectional view along line A—A of FIG. 1.

The roller therapeutic appliance 1 has an operation axis 2 and a pressure roller 3 rotatably disposed in the center of the operation axis 2. The operation axis 2, as shown in FIG. 2, has a central metal rod 4 supporting the pressure roller 3 and metal pipes 6, 6 which are fitted to both ends of the metal rod 4 and fixed by rivets 8, 8. An outer end of each metal pipe 6 is covered with a soft rubber grip 5.

The metal rod 4 is somewhat longer than the pressure roller 3, and portions of the metal rod 4 projecting from the both ends of the pressure roller 3 are fitted into metal pipes 6, 6.

Figure 3:
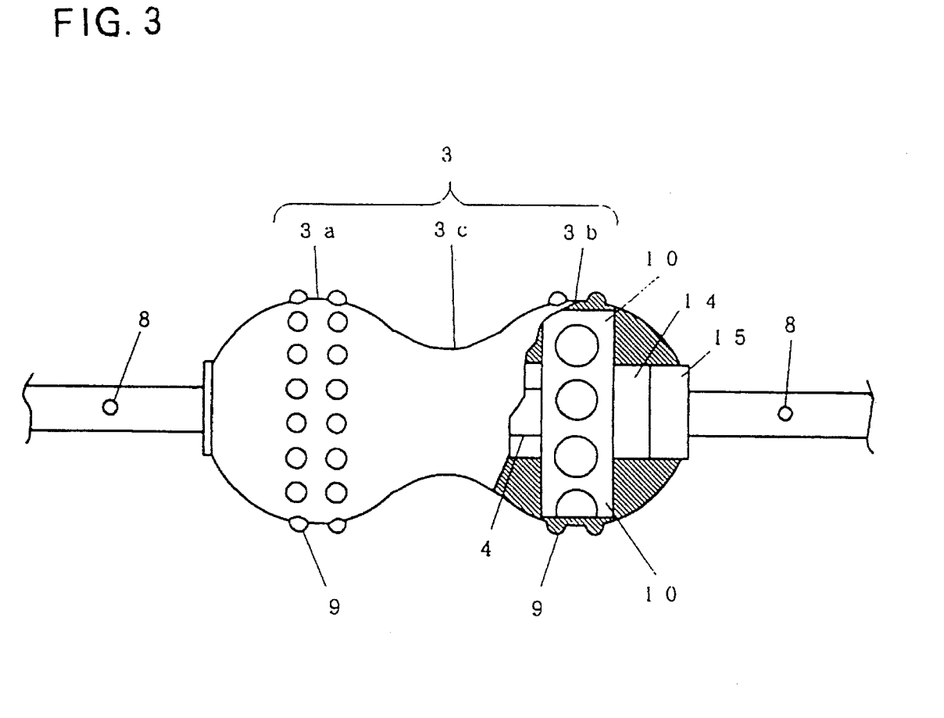
FIG. 3 is a partially broken front view showing the pressure roller.

The pressure roller 3 is an elastic material, such as a soft rubber, and includes a pair of sphere-shaped bodies 3a, 3b on either side of a centrally constricted portion 3c. Each sphere-shaped body 3a, 3b, has a plurality of semi-spheric small protrusions 9 arranged in two rows at regular intervals on their peripheral surfaces. A maximum diameter of each protrusion 9 is in contact with a human body. In each sphere-shaped body 3a, 3b, as shown in FIG. 2 and FIG. 3, annular magnetic field generating sources 10, 10 are embedded below the rows of the small protrusions 9. A hollow hole 11 has an inner diameter sufficiently larger than the diameter of the metal rod 4 of the operation axis 2, and is longitudinally situated in the pressure roller 3. The hollow hole 11 is comprised of a central portion 11a and end portions 11b, 11b, at both ends of central portion 11a. The end portions 11b, 11b each have a diameter slightly larger than that of the central portion 11a. In both end portions of the central portion 11a, the magnetic field generating sources 10, 10 are positioned. In addition, the inner diameter of the central portion 11a conforms to the inner diameter of an inner hole 13 of the magnetic field generating source 10.

The operation axis 2 is inserted into the hollow hole 11 of the pressure roller 3 and into the inner holes 13 of the magnetic field generating sources 10, 10 and the pressure roller 3 is positioned on the metal rod 4 of the operation axis 2. Bearings 15, 15 and non-skid rings 14, 14 are tightly fitted to the respective end portions 11b, 11b of the hollow hole 11. Thus, the pressure roller 3 is rotatably supported on the metal rod 4 via the bearings 15, 15. Between the inner peripheral surfaced of the pressure roller 3 and the metal rod 4 of the operation axis 2, a hollow space 12 is formed due to the central portion 11a of the hollow hole 11. The hollow space 12 permits deformation of the pressure roller 3 during use of the roller therapeutic appliance.

The non-skid ring 14 is made of synthetic resin and prevents the bearing 15 from shifting toward the central portion 11a of the hollow hole 11.

An outer portion of the bearing 15 is blocked by the non-skid ring 14 and an inner portion of it is blocked by an end face of the metal pipe 6, thus preventing the bearing 15 from shifting its position.

Figure 4:
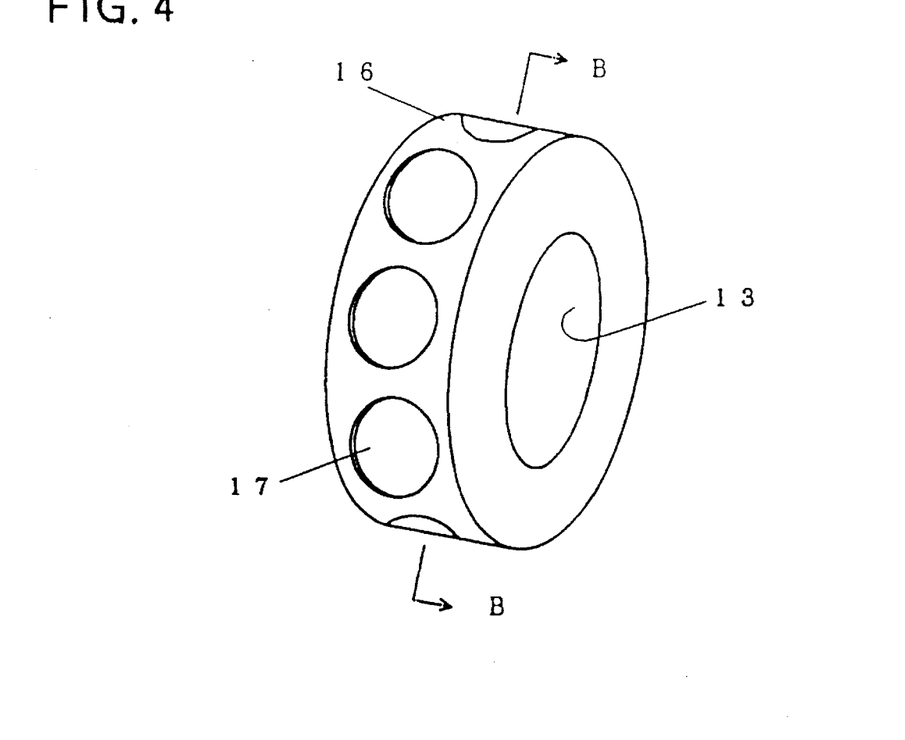
FIG. 4 is a perspective view of a magnetic field generating source.
Figure 5:
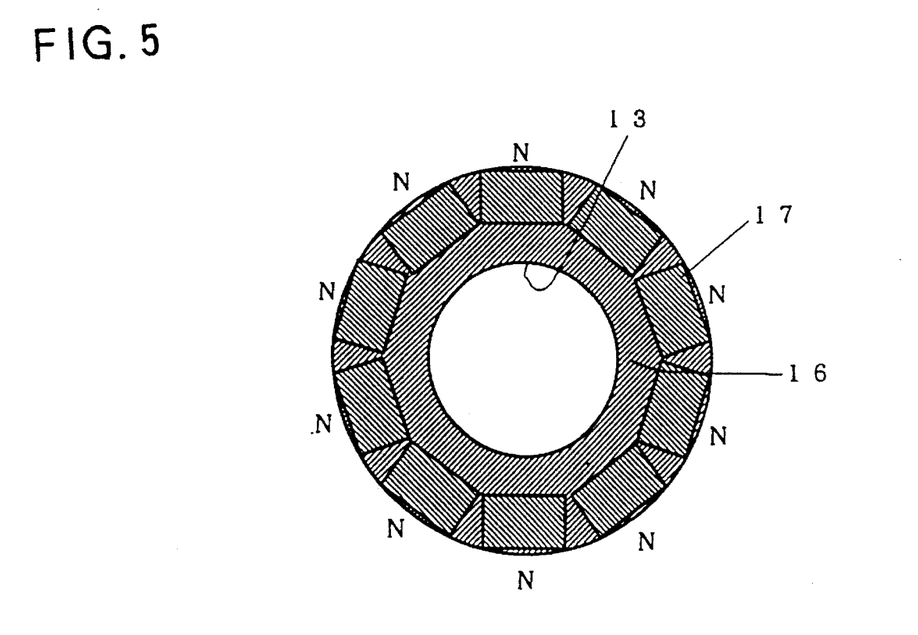
FIG. 5 is a sectional view along line B—B FIG. 4.

FIGS. 4 and FIG. 5 show a configuration of the magnetic field generating source 10.

The magnetic field generating source 10 has an outer peripheral surface of an annular metal ring 16 of a non-magnetic material such as aluminum, a plurality of mounting holes provided at regular intervals, and a cylindrical permanent magnet 17 embedded in each mounting hole. The metal ring 16 has nearly the same thickness as the width of the rows of the small protrusions 9 provided on the sphere-shaped bodies 3a, 3b, and has a smaller outer diameter than the maximum diameter of the sphere-shaped bodies 3a, 3b.

The permanent magnets 17 are embedded in the metal ring 16, with their N-poles directed outward. However, they may be embedded in the metal ring 16 with their N-poles and S-poles alternately directed outward.

Figure 6:
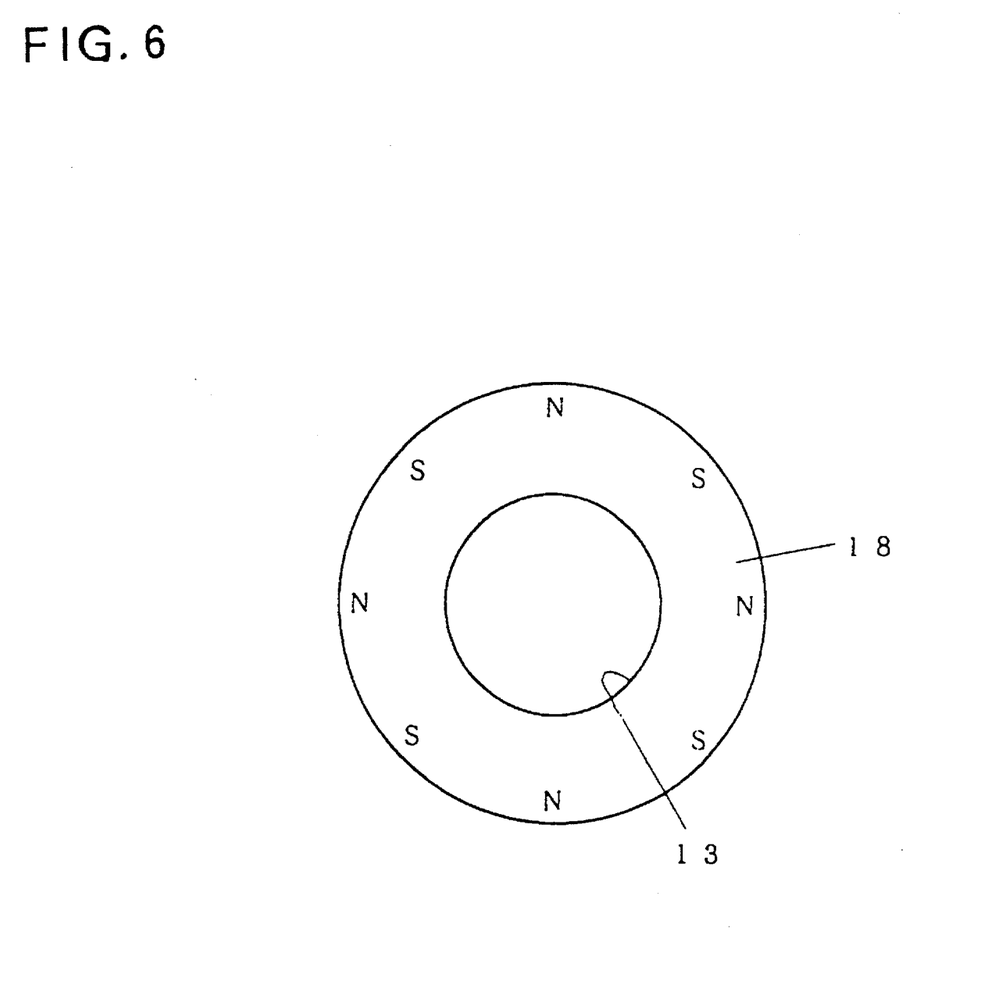
FIG. 6 is a plan view showing another embodiment of the magnetic field generating source.

In addition, as shown in FIG. 6, a magnetic field generating source 10 according to another embodiment has an annular permanent magnet 18 which is magnetized along an outer peripheral surface of the magnet.

Figure 7:
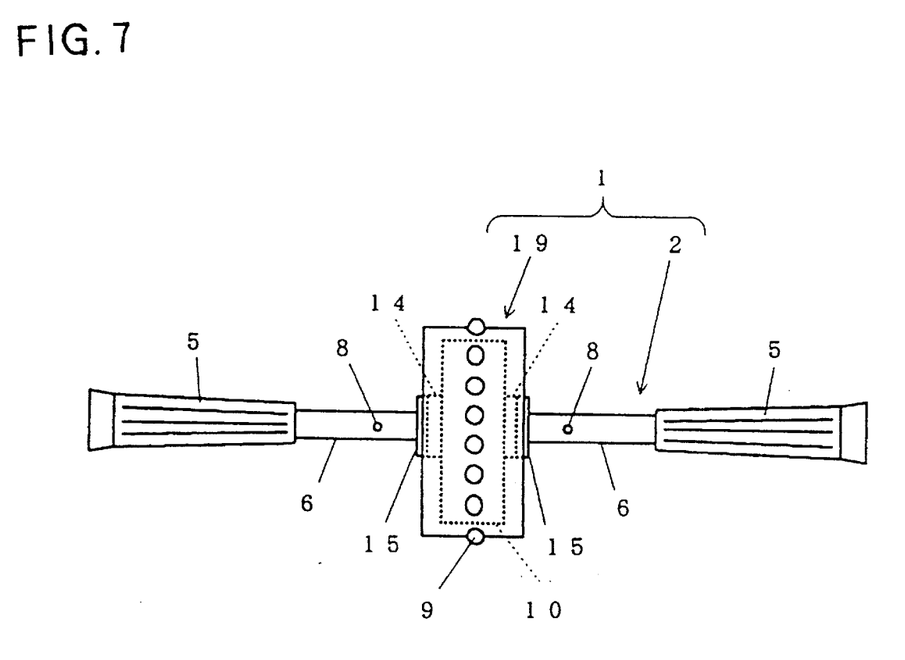
FIG. 7 is a front view of the roller therapeutic appliance of the second embodiment of the present invention.

FIG. 7 shows a roller therapeutic appliance 1 of the second embodiment of the invention.

The appliance of this embodiment has a disk-shaped pressure roller 19 and one magnetic field generating source 10 embedded below the row of the small protrusions 9 on the pressure roller 19.

Structures of this embodiment which correspond to that of the first embodiment are given the same reference numerals and explanations thereof are omitted.

Figure 8:
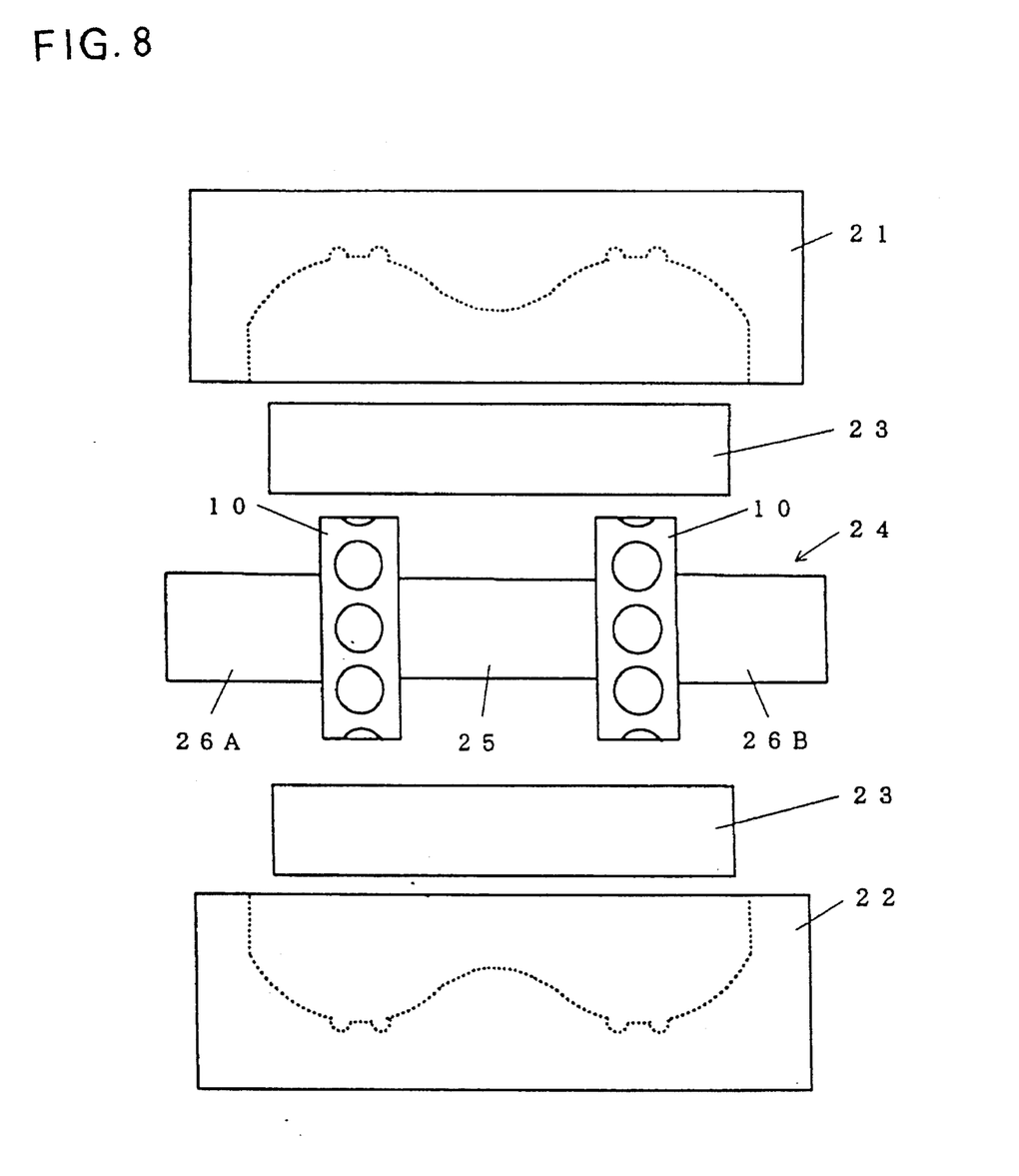
FIG. 8 is an illustration showing the method of fabricating the roller therapeutic appliance of the first embodiment.

A roller therapeutic appliance 1 according to the above-mentioned first embodiment is fabricated by serially performing the steps described in detail as follows. FIG. 8 schematically shows the process of molding the pressure roller 3.

Figure 9:
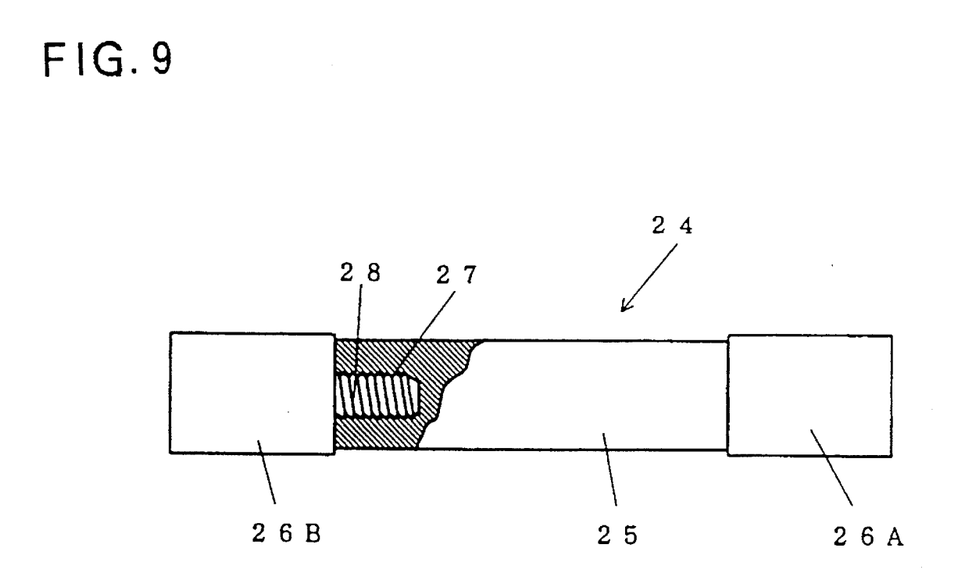
FIG. 9 is a partially broken front view of a rod-shaped jig.

In the first step, two of the magnetic field generating source 10, 10, which are to be embedded in the pressure roller 3, and a rod-shaped jig 24, shown in FIG. 9, are prepared. The jig 24 is inserted into the inner holes 13, 13 of the magnetic field generating sources 10, 10 and the magnetic field generating sources 10, 10 are supported on the jig 24, with a predetermined spacing between magnetic field generating sources 10, 10.

The rod-shaped jig 24 is longer than the pressure roller 3 and has an axis 25 which has the same outer diameter as the inner diameter of the inner hole 13 of the magnetic field generating source 10. Jig. 24 has block portions 26A, 26B, which are positioned at both ends of the axis 25 and have a larger outer diameter than that of the axis 25. One block portion 26A is integrally formed with the axis 25, while the other block portion 26B is detachably fixed to the axis 25. The block portion 26B is provided with a screw portion 28 which engages a threaded hole 27 formed at an end of the axis 25. The axis 25 has a length corresponding to a spacing between the two embedded magnetic field generating sources 10, 10.

In this process, one block portion 26B is separated from the axis 25, and the axis 25 is inserted into the inner holes 13, 13 of the magnetic field generating sources 10, 10. Thereafter, the block portion 26B is attached to the axis 25. Thereby, the magnetic field generating sources 10, 10 contact the block portions 26A, 26B to be blocked.

In the next step, the pressure roller 3 and the magnetic field generating sources 10, 10 are molded together by using a pair of die, including an upper die 21 and a lower die 22 shown in FIG. 8.

Each die 21 and 22 has a mold cavity conforming to the outer shape of the pressure roller 3. The magnetic field generating sources 10, 10 supported on the jig 24 and rubber plates 23, 23 are stacked between the dies, as shown in FIG. 8, and then the upper die 21 and the lower die 22 are closed and pressurized while heat is applied.

The rubber plates 23, 23 are deformed by heating and formed into the shape of the pressure roller 3 by the upper die 21 and the lower die 22, and thus, the magnetic field generating sources 10, 10 are embedded in the pressure roller 3.

In the third step, the jig 24 is pulled out from the molded pressure roller 3.

First, the block portion 26B, of the jig 24, projecting from one end of the pressure roller 3, is removed and separated from the axis 25. Thereafter, the axis 25 is pulled out from the other end of the pressure roller 3 by pulling the block portion 26A. A space formed in the pressure roller 3 after pulling out the jig 24 is the hollow hole 11.

In the last step, the non-skid rings 14, 14 and the bearings 15, 15 are fitted into both the end portions 11b, 11b of the hollow hole 11 of the pressure roller 3, and the metal rod 4 of the operation axis 2 is inserted into the bearings 15, 15 to rotatably support the pressure roller 3. Thereafter, the metal pipes 6, 6 are respectively fitted to both end portions of the metal rod 4 which project from the pressure roller 3. The end faces of the metal pipes 6, 6 are placed in contact with the bearings 15, 15, and then the metal pipes 6, 6 and the metal rod 4 are fixed by the rivets 8, 8.

Figure 10:
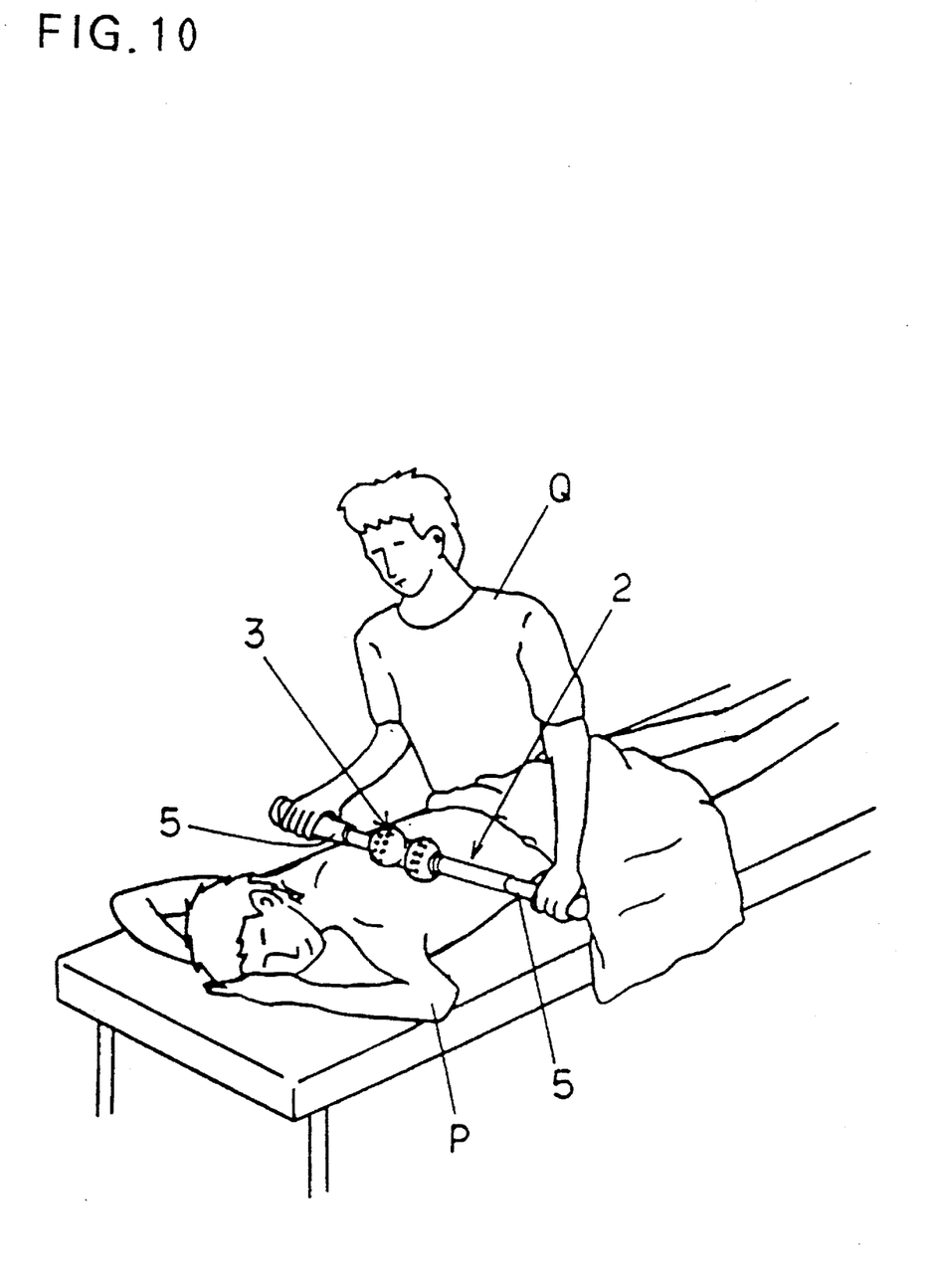
FIG. 10 is an illustration showing a method of using a roller therapeutic appliance of the first embodiment.

FIG. 10 shows a method of using the roller therapeutic appliance 1 according to the first embodiment.

First, a patient P lies facing downward, and a person Q in charge of medical treatment grasps the grips 5,5 at both ends of the operation axis 2 and applies the pressure roller 3 on the patient P's back or another part. Then, the contracted center part 3c of the pressure roller 3 is placed just above the patient P's spine. Person Q then applies pressure and rolls the roller 3 along patient P's spine. Due to this pressure, patient P's muscles along his spine are softened, and the small protrusions 9 on the pressure roller 3 press and stimulate patient P's physical points, imparting an excellent massage effect. Furthermore, magnetic lines of force generated by the magnetic field generating sources 10, 10 act on the human body to impart a magnetic therapeutic effect.

Moreover, it is possible for a patient alone to grasp the grips 5, 5 and press the pressure roller 3 on a part to be massaged and roll the roller for massaging.

In addition, the roller therapeutic appliance 1 according to the second embodiment is fabricated in the same way as the roller of the first embodiment and is used in the same manner as the roller massage appliance 1 of the first embodiment.

What is claimed is:

1. A roller therapeutic appliance comprising a longitudinal operating shaft means, a pressure roller means arranged about said operating shaft means for applying localized pressure to a body, means for rotatably supporting said pressure roller means about said shaft means, and annularly shaped magnetic field generating means molded into said pressure roller means for applying magnetic stimulation to a body, said magnetic field generating source means being adjacent an outer periphery of said pressure roller means which contacts a human body, said magnetic field generating means comprising a non-magnetic metal ring having a plurality of permanent magnets embedded, at regular intervals, along an outer peripheral surface of said non-magnetic metal ring.

2. A roller therapeutic appliance according to claim 1, wherein said pressure roller means comprises first and second spherical bodies and a relatively small diameter portion integrally connecting said first and second spherical bodies and said magnetic field generating means is molded into each of the spherical bodies.

3. A roller therapeutic appliance according to claim 1, wherein said pressure roller means comprises a disk-shaped body.

* * * * *